(12) United States Patent
Trieu

(10) Patent No.: US 7,182,783 B2
(45) Date of Patent: Feb. 27, 2007

(54) SELECTIVELY EXPANDABLE COMPOSITE STRUCTURES FOR SPINAL ARTHROPLASTY

(75) Inventor: Hai H. Trieu, Cordova, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 11/113,082

(22) Filed: Apr. 25, 2005

(65) Prior Publication Data

US 2006/0241768 A1    Oct. 26, 2006

(51) Int. Cl.
    *A61F 2/44* (2006.01)
(52) U.S. Cl. .................................................. 623/17.12
(58) Field of Classification Search ... 623/17.11–17.16
    See application file for complete search history.

(56) References Cited

U.S. PATENT DOCUMENTS

| | | | |
|---|---|---|---|
| 4,911,718 A | 3/1990 | Lee et al. | |
| 5,047,055 A | 9/1991 | Bao et al. | |
| 5,171,281 A | 12/1992 | Parsons et al. | |
| 5,192,326 A | 3/1993 | Bao et al. | |
| 5,571,191 A | 11/1996 | Fitz | |
| 5,674,295 A | 10/1997 | Ray et al. | |
| 5,824,093 A | 10/1998 | Ray et al. | |
| 5,866,113 A | 2/1999 | Hendriks et al. | |
| 5,976,186 A | 11/1999 | Bao et al. | |
| 6,022,376 A | 2/2000 | Assell et al. | |
| RE36,758 E | 6/2000 | Fitz | |
| 6,132,464 A | 10/2000 | Martin | |
| 6,264,695 B1 | 7/2001 | Stoy | |
| 6,419,704 B1 * | 7/2002 | Ferree ..................... | 623/17.12 |
| 6,419,706 B1 | 7/2002 | Graf | |
| 6,497,729 B1 * | 12/2002 | Moussy et al. .......... | 623/23.57 |
| 6,565,605 B2 | 5/2003 | Goble et al. | |
| 6,579,319 B2 | 6/2003 | Goble et al. | |
| 6,602,291 B1 * | 8/2003 | Ray et al. ................. | 623/17.11 |
| 6,610,091 B1 | 8/2003 | Reiley | |
| 6,648,893 B2 | 11/2003 | Dudasik | |
| 6,660,827 B2 | 12/2003 | Lommis et al. | |
| 6,692,528 B2 * | 2/2004 | Ward et al. .............. | 623/17.12 |
| 6,764,514 B1 * | 7/2004 | Li et al. ................... | 623/17.12 |
| 6,783,546 B2 * | 8/2004 | Zucherman et al. ..... | 623/17.16 |
| 6,893,466 B2 * | 5/2005 | Trieu ....................... | 623/17.16 |
| 2002/0026244 A1 | 2/2002 | Trieu | |
| 2002/0065557 A1 | 5/2002 | Goble et al. | |
| 2002/0123806 A1 | 9/2002 | Reiley | |
| 2003/0004572 A1 | 1/2003 | Goble et al. | |
| 2003/0023311 A1 | 1/2003 | Trieu | |
| 2003/0191532 A1 | 10/2003 | Goble et al. | |
| 2003/0199984 A1 | 10/2003 | Trieu | |
| 2003/0204259 A1 | 10/2003 | Goble et al. | |
| 2004/0006391 A1 | 1/2004 | Reiley | |
| 2004/0049272 A1 | 3/2004 | Reiley | |
| 2004/0049273 A1 | 3/2004 | Reiley | |

(Continued)

Primary Examiner—Suzette Gherbi
(74) Attorney, Agent, or Firm—Hunton & Williams LLP

(57) ABSTRACT

Embodiments include selectively expandable composite structures useful as spinal arthroplasty devices such as intervertebral disc prostheses. The structures may comprise an outer shell comprised of a non-hydrogel polymer material. The structures also may comprise at least one core positioned within the outer shell. The core may be comprised of a hydrophilic polymer. The core may expand upon hydration, thereby deforming the outer shell. The selectively expandable composite structures may be implanted in a dehydrated form and then expand during re-hydration following implantation.

39 Claims, 5 Drawing Sheets

U.S. PATENT DOCUMENTS

| | | |
|---|---|---|
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049281 A1 | 3/2004 | Reiley |
| 2004/0111154 A1 | 6/2004 | Reiley |
| 2004/0186471 A1* | 9/2004 | Trieu .......................... 606/61 |
| 2005/0027361 A1 | 2/2005 | Reiley |
| 2005/0043797 A1 | 2/2005 | Lee |
| 2005/0043799 A1 | 2/2005 | Reiley |
| 2005/0055096 A1 | 3/2005 | Serhan et al. |
| 2005/0154463 A1* | 7/2005 | Trieu ....................... 623/17.16 |
| 2005/0171611 A1* | 8/2005 | Stoy et al. ................ 623/17.16 |
| 2005/0203206 A1* | 9/2005 | Trieu .......................... 523/113 |
| 2005/0267577 A1* | 12/2005 | Trieu ....................... 623/17.11 |
| 2005/0278029 A1* | 12/2005 | Trieu ....................... 623/17.16 |

\* cited by examiner (A)

(B)

(C)

(D)

SELECTIVELY EXPANDABLE COMPOSITE STRUCTURES FOR SPINAL ARTHROPLASTY

FIELD OF THE INVENTION

Embodiments of the invention relate to selectively expandable composite structures for spinal arthroplasty, such as intervertebral disc prostheses. More specifically, the selectively expandable composite structures are capable of water uptake and preferential swelling so that the implant will expand at desired locations.

BACKGROUND

The human spine includes intervertebral discs that are located between adjacent vertebrae of the spine. The intervertebral discs function to stabilize the spine and distribute forces between vertebrae. Intervertebral discs generally comprise three regions, known as the annulus fibrosis, the nucleus pulposus, and the cartilagenous, or bony, end plates.

The nucleus pulposus retains a gelatinous consistency, and includes a high proteoglycan content. The nucleus pulposus further retains approximately 70% to 90% water, aiding in its fluid nature. The nucleus pulposus is contained within the annulus fibrosis. The annulus fibrosis retains a more rigid consistency, and is composed primarily of type I and type II collagen. The annulus fibrosis functions to provide peripheral mechanical support to the intervertebral discs, torsional resistance, and resistance to the hydrostatic pressures of the nucleus pulposus.

Intervertebral discs may be displaced or damaged due to trauma or disease. Disruption of the annulus fibrosis may allow the nucleus pulposus to protrude into the vertebral canal, a condition commonly referred to as a herniated or ruptured disc. The extruded nucleus pulposus may press on a spinal nerve, resulting in nerve damage, pain, numbness, muscle weakness, and paralysis. Intervertebral discs also may deteriorate due to the normal aging process. As a disc dehydrates and hardens, the disc space height may be reduced, leading to instability of the spine, decreased mobility, and pain.

One way to relieve the symptoms of these conditions is by surgical removal of a portion or all of the intervertebral disc. The removal of the damaged or unhealthy disc may allow the disc space to collapse, which could lead to instability of the spine, abnormal joint mechanics, nerve damage, and as severe pain.

Researchers therefore have investigated the efficacy of implanting an intervertebral disc prosthesis to replace the damaged portion of the patient's intervertebral disc. One such prosthesis is an artificial implantable nucleus replacement device. Nucleus implants are used when the nucleus pulposus of the intervertebral disc is damaged but the annulus fibrosis and vertebral end-plates are still sufficiently healthy. Nucleus replacement surgery involves removing the damaged nucleus pulposus of the intervertebral disc and insertion of the nucleus implant inside of the retained annulus fibrosis. The nucleus implant can be a molded polymer-containing device designed to absorb the compressive forces placed on the spine. For increased strength, the nucleus implant may be combined with an internal matrix of, for example, bio-compatible fibers. The retained annulus fibrosis provides tensile strength. Some desirable attributes of a hypothetical intervertebral disc prosthesis include axially compressibility for shock absorbance, excellent durability to avoid future replacement, and biocompatibility.

The description herein of problems and disadvantages of known apparatus, methods, and devices is not intended to limit the invention to the exclusion of these known entities. Indeed, embodiments of the invention may include one or more of the known apparatus, methods, and devices without suffering from the disadvantages and problems noted herein.

SUMMARY OF THE INVENTION

What is needed are improved spinal arthroplasty devices. In particular, an improved intervertebral disc prosthesis is needed. Additionally, an intervertebral disc prosthesis that can better conform to the intervertebral disc space is needed. Embodiments of the invention solve some or all of these needs, as well as additional needs.

Therefore, in accordance with an embodiment of the present invention, there is provided a selectively expandable composite intervertebral disc prosthesis. The prosthesis comprises an outer shell that is comprised of a non-hydrogel polymer material. Additionally, the prosthesis comprises at least one core positioned within the outer shell, wherein the core is comprised of a hydrophilic polymer. The at least one core may expand upon hydration, thereby deforming the outer shell.

In accordance with another embodiment of the present invention, there is provided a method of treating or preventing a disease or disorder associated with the spine. The method comprises providing a selectively expandable composite intervertebral disc prosthesis as described herein. The prosthesis may be substantially dehydrated and inserted into an intervertebral disc space. Following insertion, the prosthesis may be allowed to re-hydrate in the intervertebral disc space.

These and other features and advantages of the present invention will be apparent from the description provide herein.

DETAILED DESCRIPTION OF THE EMBODIMENTS

Figure 1:
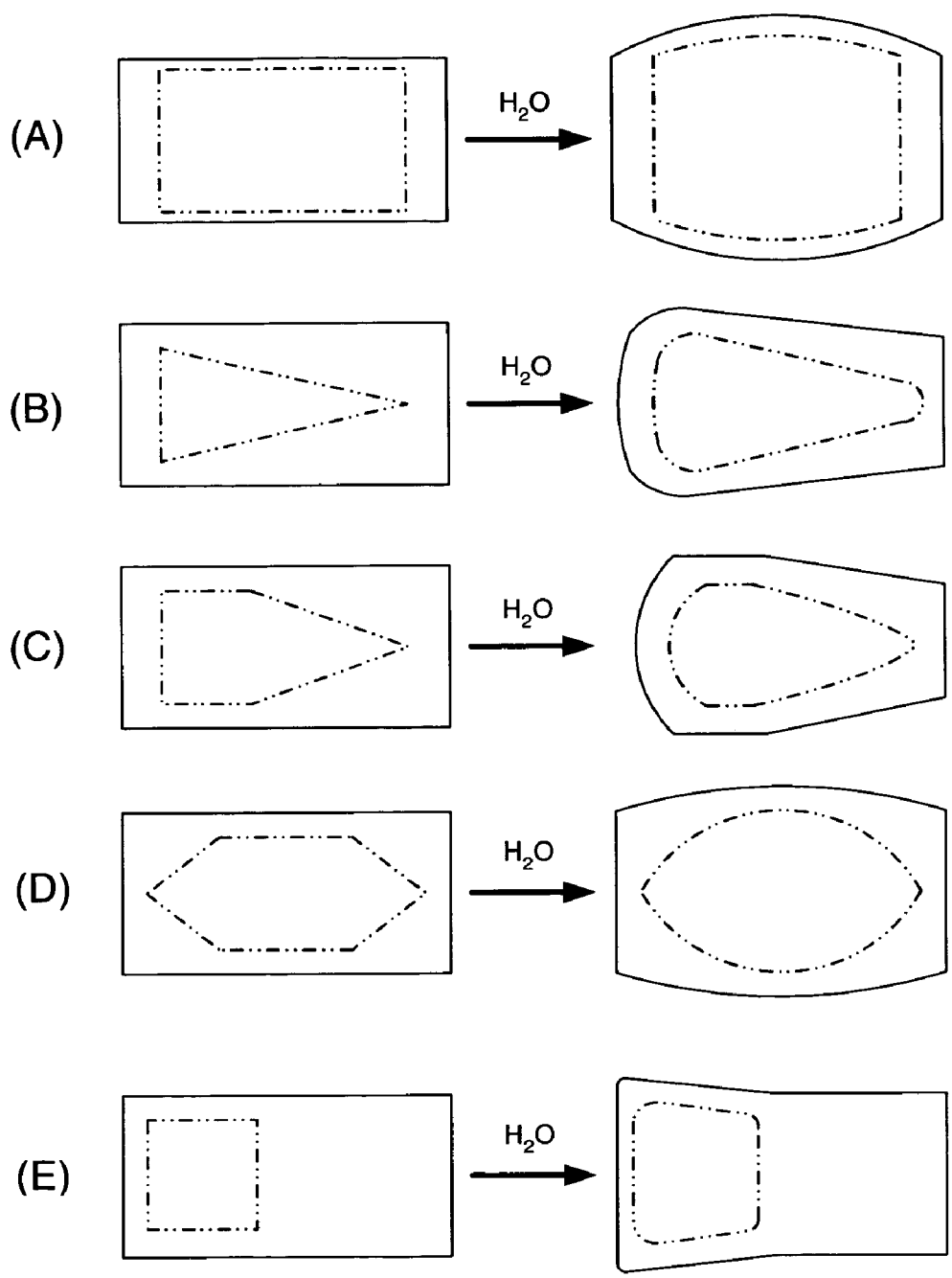
FIG. 1, embodiments A–E, is a drawing of exemplary selectively expandable composite intervertebral disc prostheses according to embodiments of the invention.

The following description is intended to convey a thorough understanding of the various embodiments of the invention by providing a number of specific embodiments and details involving selectively expandable composite structures for spinal arthroplasty. It is understood, however, that the present invention is not limited to these specific embodiments and details, which are exemplary only. It is further understood that one possessing ordinary skill in the art, in light of known systems and methods, would appreciate the use of the invention for its intended purposes and benefits in any number of alternative embodiments.

As used throughout this disclosure, the singular forms "a," "an," and "the" include plural reference unless the context clearly dictates otherwise. Thus, for example, a reference to "a spinal implant" includes a plurality of such implants, as well as a single implant, and a reference to "a therapeutic agent" is a reference to one or more therapeutic and/or pharmaceutical agents and equivalents thereof known to those skilled in the art, and so forth.

As used throughout this description, the expression "selectively expandable" means that the device comprising an outer shell and at least one core positioned within the outer shell expands in a non-uniform fashion upon hydration. The non-uniform expansion, for example, may be caused by the outer shell constraining the ability of the at least one core to expand, resulting in preferential expansion in one or more directions. "Selectively expandable" devices excludes devices such as the tapered prosthesis described in U.S. Pat. No. 6,132,465.

As used throughout this description, the expression "non-hydrogel polymer material" denotes any polymer composition that is capable of forming a substantially solid mass, and that is not comprised of a hydrogel polymer. The non-hydrogel polymer materials are capable of absorbing less than about 5% by weight of water.

Throughout this description, the term "hydrogel" denotes a polymeric material that is capable of absorbing water up to and including its equilibrium water content. Hydrogels include conventional hydrogel materials, as well as xerogel materials, including those disclosed in, for example, U.S. Pat. Nos. 5,047,055, 5,192,326, 5,976,186, 6,264,695, 6,660,827, and 6,726,721, the disclosures of each of which are incorporated by reference herein in their entirety.

The expression "hydrophilic polymer" refers to a polymer that is capable of absorbing more than about 10% by weight of water.

Throughout this description, the term "intervertebral disc space" refers to any volume or void between two adjacent vertebrae. The intervertebral disc space may be the volume inside of the annulus fibrosis of the intervertebral disc. Alternatively, the intervertebral disc space also may include the annulus fibrosis itself. The intervertebral disc space may include only a portion or the entire volume or void between two adjacent vertebrae.

Unless defined otherwise, all other technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the various spinal implants, therapeutic and/or pharmaceutical agents, and other components that are reported in the publications and that might be used in connection with embodiments of the invention. Nothing herein is to be construed as an admission that the invention is not entitled to antedate such disclosures by virtue of prior invention.

It is a feature of an embodiment of the present invention to provide selectively expandable composite structures comprising an outer shell of a non-hydrogel polymer material, and at least one core positioned within the outer shell. The core may be comprised of a hydrophilic polymer. The at least one core may expand upon hydration, thereby deforming the outer shell. In this way, the selectively expandable composite structures can be implanted in a dehydrated form and then attain an expanded form due to hydration following implantation. The selectively expandable composite structures are useful, for example, as spinal arthroplasty devices such as intervertebral disc prostheses, including nucleus replacements.

The selectively expandable composite structures may be in any desired shape, in accordance with the guidelines herein. Preferably, the composite structures are shaped to function as intervertebral disc implants or devices. For example, the composite structure's cross-sectional shape may be kidney-shaped, C-shaped, oval-like, spherical, rectangular, square, cylindrical, capsule, U-shaped, V-shaped, X-shaped, "O" or donut shaped, and so forth in order to conform to the natural cross-sectional shape of the intervertebral disc space. Additionally, the structures may be any applicable size, in accordance with the guidelines herein, and preferred sizes are described herein.

The outer shell of the selectively expandable composite structures may be comprised of at least one non-hydrogel polymer material. Preferably, at least one of the non-hydrogel polymer materials comprising the outer shell is an elastic material. An elastic component of the outer shell may be desirable because it may enhance deformation of the outer shell when the core expands due to hydration. Some suitable non-hydrogel polymer materials for use in the outer shell include elastomeric materials, olefin polymers, and thermoplastic silicone polyurethane copolymers. To the extent that these materials are capable of absorbing more than about 5% by weight of water, they can be modified by, for example, cross-linking, etc., to reduce their water absorbing ability to within the range described herein so as to constitute a non-hydrogel polymer material.

Suitable elastomeric materials include silicone, polyurethanes, silicone polyurethane copolymers, polyolefins, thermoplastic elastomers, thermoset elastomers, thermoplastic polymers, thermoset polymers, and combinations thereof, such as copolymers. Suitable polyolefins include polyisobutylene rubber and polyisoprene rubber, neoprene rubber, nitrile rubber, vulcanized rubber, and combinations thereof. The vulcanized rubber described herein may be produced, for example, by a vulcanization process utilizing a copolymer produced as described, for example, in U.S. Pat. No. 5,245,098, from 1-hexene and 5-methyl-1,4-hexadiene.

Suitable olefin polymers also include polymers made from ethylenically unsaturated monomers, such as polybutadiene. Olefin polymers typically require a polymerization catalyst to form the polymer, and polymers derived from ethylenically unsaturated monomers typically require a light or heat activated catalyst to polymerize the polymer. Thermoplastic silicone polyurethane copolymers are particularly preferred elastomeric materials for use in the invention.

Examples of thermoplastic silicone polyurethane copolymers useful as elastomeric materials include, but are not limited to, silicone polyetherurethanes; silicone polycarbonateurethane; silicone poly(tetramethylene-oxide) (PTMO) polyether-based aromatic silicone polyurethanes; silicone PTMO polyether-based aliphatic polyurethanes; silicone polyurethane ureas; and mixtures and combinations thereof. Suitable thermoplastic silicone polyurethane copolymers are commercially available, and non-limiting commercially available, suitable thermoplastic silicone polyurethane copolymers comprise, or alternatively consist of, PurSil (including PurSil-10, -20, and -40) (available from Polymertech, Berkley, Calif.), CarboSil (including CarboSil-10, -20, and -40) (available from Polymertech, Berkley, Calif.), Elast-Eon silicone polyurethanes with silicone content between 10% and 50% (available from Aortech Biomaterials, Victoria, Australia), and combinations thereof. Thermoplastic silicone polyurethane copolymers used in the generation of selectively expandable composite structures may be non-biodegradable.

In a preferred embodiment, the outer shell may have a differential composition. In other words, the outer shell may be comprised of at least one non-hydrogel polymer material mixed or combined with one or more other polymeric materials, including other non-hydrogel polymer materials. The composition may be varied depending upon the position or location in the outer shell in order to provide differential properties to the outer shell. For example, the outer shell can be made more malleable or flexible at its upper and lower surfaces and less malleable or flexible along its periphery by varying the composition of the outer shell, for example, by using more elastic polymers at its upper and lower surfaces and less elastic polymers at its periphery. Doing so may facilitate the selective or preferential expansion of the device upon hydration of its core.

Because the outer shell may comprise at least one polymeric material, at least one of which is elastic, the outer shell may possess an intrinsic volume, regardless of the state of hydration of the selectively expandable composite implant. In a preferred embodiment, the hydrophilic polymer that comprises the core is no more than about 75%, and more preferably no more than about 60%, and most preferably no more than about 50% of the total volume of the selectively expandable composite structure in its de-hydrated state. This may be advantageous because, were the composite structure to de-hydrate in situ, at least the outer shell would retain its intrinsic volume, and therefore the composite structure may continue to at least partially support the disc space height and articulation of the vertebrae between which it is implanted. Comparatively, a composite structure where the volume primarily is a function of the hydrophilic polymer may almost completely deflate if it were to de-hydrate in situ, possibly leading to catastrophic disk collapse and other inappropriate disc mechanics. In another preferred embodiment, the increase in volume of the selectively expandable composite structure is no more than about 3 times, more preferably no more than about 2.5 times, and most preferably no more than about 2 times the de-hydrated volume. Therefore, were the composite structure to de-hydrate in vivo, the structure still may retain at least half of its hydrated volume, which may help to prevent catastrophic disc collapse and failure.

Nevertheless, an increase in volume via hydration following implantation may be useful, for example, in order to improve the fit and geometry of the selectively expandable composite structure. Preferably, the composite structure may be implanted with a volume and/or height at least slightly less than the volume and/or height of the intervertebral disc space. This may facilitate insertion of the composite structure by ensuring that the dimensions of the composite structure are such that they it can fit within the confines of the intervertebral disc space. Upon implantation, the structure preferably hydrates by absorbing water from surrounding bodily fluids or applied solutions and, because the core comprises a hydrophilic polymer, the composite structure expands. The expansion of the composite structure preferably may result in the structure filling at least 90%, more preferably at least 95%, even more preferably at least 99%, and most preferably at least 100% of the volume of the intervertebral disc space into which it is implanted. Also, when expanded, the composite structure preferably at least equals the width and height of the natural disc space. In some instances where disc space height is to be restored, the expanded composite implant preferably increases the disc height by pushing on the vertebral endplates of the adjacent vertebrae. Generally, a structure that expands upon implantation, such as the composite structures herein, may lead to improved fit and geometry of the structure, in turn leading to increased maximum load-bearing, stress transfer, and bonding of the structure to the intervertebral disc space.

Besides increasing the volume of the selectively expandable composite structure, the core may be useful to absorb the load and shock placed upon the prosthesis when implanted between adjacent vertebrae. For example, as the hydrophilic polymer(s) that comprise the core expand during hydration, the core may become more compliant as a result of its water uptake. A more compliant core may serve to more readily absorb the stresses placed on the composite structure. This may be advantageous to simulate or imitate the functioning of the endogenous intervertebral disc.

The ability of the composite structure to expand upon hydration may be a function of the hydrophilic polymers that comprise the at least one core. Hydrophilic polymers useful in forming the expandable composite structures of embodiments of the invention include any applicable now known or later discovered hydrophilic polymers that are capable of absorbing more than about 10% by weight of water, preferably more than about 15% by weight of water, and more preferably more than about 50% by weight of water, in accordance with the guidelines provided herein. Some exemplary materials for use in the at least one core include hydrogels and polyelectrolytes. To the extent that these materials are capable of absorbing less than about 10% by weight of water, they can be modified to increase their water absorbing ability to within the range described herein, so as to constitute a hydrophilic polymer. In an alternative embodiment, the core may comprise more than one hydrophilic polymer. The hydrophilic polymers may be present in the core as a blend, mixture, or in a heterogeneous configuration.

Non-limiting examples of hydrophilic polymers include, but are not limited to, polyacrylamide; polyacrylic acid; polyvinylpyrrolidone; copolymers of ethyleneoxide and propyleneoxide or hyaluronic acid; naturally-occurring materials such as collagen, gelatin, albumin, keratin, elastin, silk, hyaluronic acid and derivatives thereof, proteoglycan, glucomannan gel, and polysaccharides such as cross-linked carboxyl-containing polysaccharides; and combinations thereof.

In another preferred embodiment, polyelectrolytes can be used as the hydrophilic polymer that comprises the at least one core, or are added in combination with the hydrophilic polymer to further enhance the hydrophilic nature of the core of the expandable composite structures. Non-limiting examples of polyelectrolytes that may be added to or alternatively comprise the core of hydrophilic polymer include, but are not limited to, members of the following systems: proteins, nucleic acids, sulfonated styrene, polyacrylic acids, polymethacrylic acid, polystyrene sulfate, carboxymethylcellulose, Xantham gum, pectins, polyallylamine hydrochloride, carrageenan, and mixtures and combinations thereof. Polyelectrolytes are well known in the art, and one skilled in the art will appreciate still other examples of polyelectrolytes that may be used in the embodiments described herein.

Polyelectrolytes may be added to the hydrophilic polymer in concentrations comprising, or alternatively consisting of, about 5–100% by weight of the hydrophilic polymer, when used in combination with another hydrophilic polymer. The polyelectrolyte preferably is present in an amount ranging from about 5–25% (by weight), based on the weight of the hydrophilic polymer.

In another embodiment, the hydrophilic polymer may be a hydrogel. Suitable hydrogels include natural hydrogels and those formed from polyvinyl alcohol; polyacrylamides; polyacrylic acid; poly(acrylonitrile-acrylic acid); polyurethanes; polyethylene glycol; polyethyleneoxide; poly(N-vinyl-2-pyrrolidone); polyacrylates such as poly(2-hydroxy ethyl methacrylate) and copolymers of acrylates with N-vinyl pyrrolidone; N-vinyl lactams; acrylamide; polyurethanes; other similar materials that form a hydrogel; and combinations thereof. The hydrogel materials further may be cross-linked to provide additional strength to the outer shell.

In another preferred embodiment, additives may be added to the hydrophilic polymer in order to modify or enhance the water absorption behavior of the core. For example, additives such as sodium chloride, calcium chloride, magnesium chloride, magnesium sulfate, potassium sulfate, potassium chloride, sodium sulfate, sodium acetate, ammonium phosphate, ammonium sulfate, calcium lactate, magnesium succinate, sucrose, glucose, and fructose may be added to the hydrophilic polymer in the core in order to increase the hydrophilicity of the core.

The at least one core comprising a hydrophilic polymer may be present in any number of physical configurations, including a single piece, multiple pieces, chunks, granules, flakes, pellets, cylinders, strips, spheres, microspheres, powders, beads, capsules, and particulates. Additionally, the core may be mixtures and combinations of these different physical configurations. For example, the core may comprises multiple solid pieces mixed with granules, which may fill the voids in between the multiple solid pieces. Furthermore, the core may be either solid or porous. For example, if the core comprises multiple pieces, the multiple pieces may individually be solid or porous pieces. A porous or semi-porous core may be desirable to serve as a reservoir for therapeutic agents, pharmaceutical agents, growth factors, and radiopaque agents. Preferably, if at least a portion of the core is porous, the porous portion comprises no more than about 75% by volume of voids, more preferably no more than about 60% by volume of voids, and most preferably no more than about 50% by volume of voids.

If desired, the core may be formed before, during, or after implantation of the outer shell. For example, the core typically may be implanted with the outer shell (i.e. the core is already positioned within the outer shell when the outer shell is delivered to the implant site). However, in some instances it may be desirable to implant the outer shell portion of the selectively expandable device separately from the at least one core. Then, the at least one core may be delivered inside of the outer shell. For example, the hydrophilic polymer(s) that comprise the core may be delivered by cannula into the interior of the outer shell, for example, through a collapsible valve positioned in the outer shell. The hydrophilic polymer advantageously may be heated in order to reduce its viscosity in preparation of delivery to the interior of the outer shell. Subsequent delivery of the hydrophilic polymer comprising the core after implantation of the outer shell may be desirable in order to reduce the cross-section of the device during implantation. By implanting the device as two separate components, each having a cross-section smaller than the whole, delivery of the device to the confines of the intervertebral disc space may be facilitated.

In another embodiment of the invention, the selectively expandable composite structures may assume any appropriate geometry or size for implantation into the intervertebral disc space. For example, the selectively expandable composite structures preferably may be from about 3 mm to about 15 mm in height so as to accommodate a range of intervertebral disc space heights. The selectively expandable composite structures also preferably may range in volume from about 0.5 milliliters to about 8 milliliters in a hydrated state so as to accommodate a range of intervertebral disc space volumes. One who is skilled in the art will appreciate the myriad geometries and sizes that the selectively expandable composite structures may take, in accordance with the guidelines herein.

In a preferred embodiment, the outer shell may be designed so that water can penetrate through the outer shell to reach the at least one core of hydrophilic polymer positioned within the shell. Penetration of water to the at least one core may be desirable because hydration of the core may cause it to expand, thereby deforming the outer shell in a selective manner and increasing the overall volume of the composite structure. Penetration of water to the at least one core may occur in any applicable fashion according to the guidelines herein, and several exemplary methods are described herein.

In one example, it may be preferred that the outer shell comprise a hydrophilic component mixed with the non-hydrogel polymer material. By absorbing moisture from the environment surrounding the selectively expandable composite structure, the hydrophilic component of the outer shell can deliver water to the at least one core positioned within the shell. Preferably, the hydrophilic component in the outer shell may be from about 1% to about 25% by weight of the mixture of non-hydrogel polymer material and hydrophilic component. The hydrophilic polymers, including polyelectrolytes and hydrogels, described herein in relation to the hydrophilic core also are suitable hydrophilic components for use in the outer shell.

In another preferred embodiment, the outer shell may comprise a plurality of perforations of sufficient size and number to permit fluids to percolate through the shell and contact at least a portion of the at least one core. The perforations in the outer shell may be described as slits or cuts. Preferably, the perforations are of sufficient depth to contact or even extend into the at least one core positioned with the outer shell. In this manner, a physical pathway may be provided so that fluids in the environment surrounding the composite structure can penetrate to and hydrate the at least one core.

The outer shell also may be at least partially porous in preferred embodiments of the invention. Again, pores in the shell may provide physical routes for fluids to penetrate to and hydrate the at least one core. The pores may be located throughout the outer shell or may be positioned only in portions of the shell that are adjacent to cores positioned within the shell. Also, the density and depth of pores in the shell may vary by location or position. For example, pores may be concentrated and deeper in portions of the shell adjacent to the hydrophilic cores that are to be hydrated.

Any pores or, alternatively, perforations in the outer shell of the selectively expandable composite structures preferably are sized in such a manner as to preclude migration of the core material outside of the composite structure. For example, if the material comprising the core is granular in nature, the pores or perforation in the outer shell preferably are small enough to prevent migration of the granular core material outside of the composite structure. This applies equally to a core, for example, comprising a solid piece, multiple solid pieces, several chunks, granules, flakes, pellets, cylinders, strips, spheres, microspheres, powders, or mixtures and combinations thereof.

Figure 5:
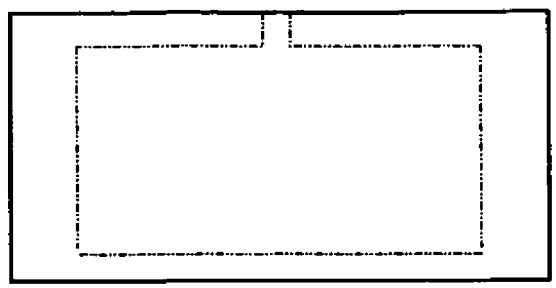
FIG. 5, embodiments A, B, and C, is a drawing of an exemplary selectively expandable composite intervertebral disc prosthesis.
Figure 5:
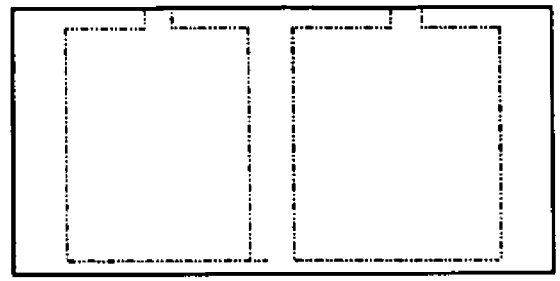
Figure 5:
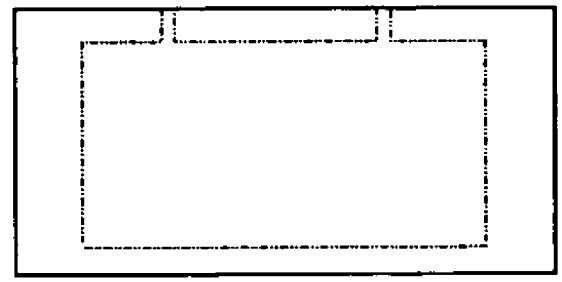
Figure 5:
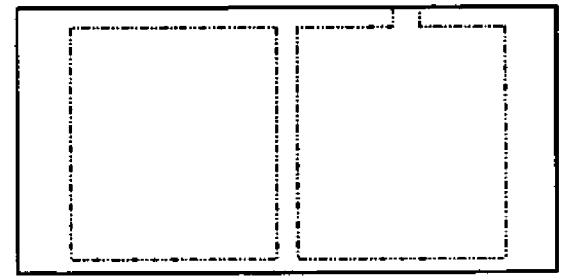

The composite structures also may comprise at least one conduit that connects the at least one core with a surface of the prosthesis. The conduits may comprise a hydrophilic polymer. Preferably, the conduits may comprise the same hydrophilic polymer of which the at least one core is comprised. The conduits may provide a route by which moisture may be wicked from the environment surrounding the composite structure to the at least one core positioned within the outer shell. Exemplary conduits are illustrated in FIG. 5, embodiments A, B, and C. As can be seen, the cores are connected to the surface of the device by one or more conduits of hydrophilic material. Preferably, as in embodiment B, each core (if more than one) within the outer shell is connected by a conduit to the surface of the device. If desired, more than one conduit may connect a core to the surface (e.g. embodiment C). Also, if desired, some cores may be connected by conduits, whereas others are not (e.g. embodiment D). The conduits may enhance fluid exchange with the environment in order to accelerate hydration of the core(s) within the outer shell.

Upon hydration, the composite structures preferably expand in a selective manner. The selective expansion of the composite structures may depend upon several different variables, including the type of hydrophilic polymer that comprises the at least one core; the type of non-hydrogel polymer material that comprises the outer shell; the concentrations of non-hydrogel polymer material and hydrophilic material, respectively, in the outer shell and the at least one core; the shape of the outer shell and the at least one core; the position(s) within the outer shell at which the at least one core is located; and so forth. In a preferred embodiment, these variables may be controlled in order to produce swelling or expansion of the composite structures upon hydration in selected areas or portions of the structures. In this way, the final configuration of the expanded structure can be controlled to produce a desired configuration, topography, geometry, or shape. For example, expansion can be controlled so that the anterior portion of a composite structure to be used as an intervertebral disc prosthesis expands more than the posterior portion. A selectively expandable intervertebral disc prosthesis with preferential anterior expansion may be useful to correct or preserve lordosis of the spine.

In a preferred embodiment, the composite structures provided by embodiments of the invention are configured to function as intervertebral disc prostheses, such as nucleus replacements and replacements for the entire intervertebral disc. Intervertebral disc prostheses according to this embodiment optionally may comprise supplemental components, such as vertebral endplate contacting elements, in order to increase their utility for treating disorders of the spine.

FIG. 1, embodiments A–E, illustrates exemplary intervertebral disc prostheses according to embodiments of the invention. The views illustrated are cross-sections of intervertebral disc prostheses and illustrate how placement, size, and shape of the hydrophilic core can affect the expansion of the composite structure upon hydration. Embodiments B, C, and E, for example, illustrate selectively expandable composite structures that are useful for the correction and maintenance of spinal curvature because one end of the prosthesis expands to a greater height than does the other end. In embodiments B and C, for example, the selective expansion is due to the shape of the hydrophilic core. In embodiment E, the selective expansion is due to the placement of the hydrophilic core at one end only of the composite structure.

Embodiments A and D illustrate selectively expandable composite structures that are useful for engagement with hemispherical vertebral endplates because they have a greater height at the center of the structure than at the periphery. As can be seen in embodiment A, this may be the result of the outer shell being thinner at the top and bottom of the composite structure, but thicker on the sides or periphery of the composite structure. Also, as can be seen in embodiment D, this may be the result of the dome-like shape of the hydrophilic core within the outer shell. Selectively expandable composite structures having either concave or convex top and bottom surfaces may be useful for mating with convex or concave surfaces, respectively, of upper and lower vertebral endplates between which the selectively expandable composite structures are to be positioned. For example, Embodiments A and D illustrate selectively expandable composite structures having convex upper and lower surfaces. Therefore, these structure may be appropriate for implantation between upper and lower vertebral endplates having concave surfaces.

In another embodiment, the selectively expandable composite structures, when in a de-hydrated state, have a size and geometry primarily dictated by the size and geometry of the outer shell of the composite structures. Therefore, as illustrated in FIG. 1, embodiments A–E, the exemplary composite structures are all rectangular in profile in their de-hydrated state. However, upon hydration, the outer shell preferably is selectively deformed according to the shape of the hydrophilic inner core. Therefore, as illustrated in FIG. 1, the outer shells of the exemplary composite structures, upon hydration, are deformed according to the shape of the inner cores. For example, the inner core in embodiment B is triangular in profile and causes the outer shell, upon hydration, to deform into a more triangular shape. In other words, in a preferred embodiment the shape of the composite structures upon hydration in part may be determined by the shape of the inner core, among other factors. Preferably, the shape of the composite structure in its de-hydrated state corresponds to a preferred insertion configuration, and the shape of the composite structure in its hydrated state corresponds to a preferred configuration for long-term placement and funcationality in the intervertebral disc space.

Figure 2:
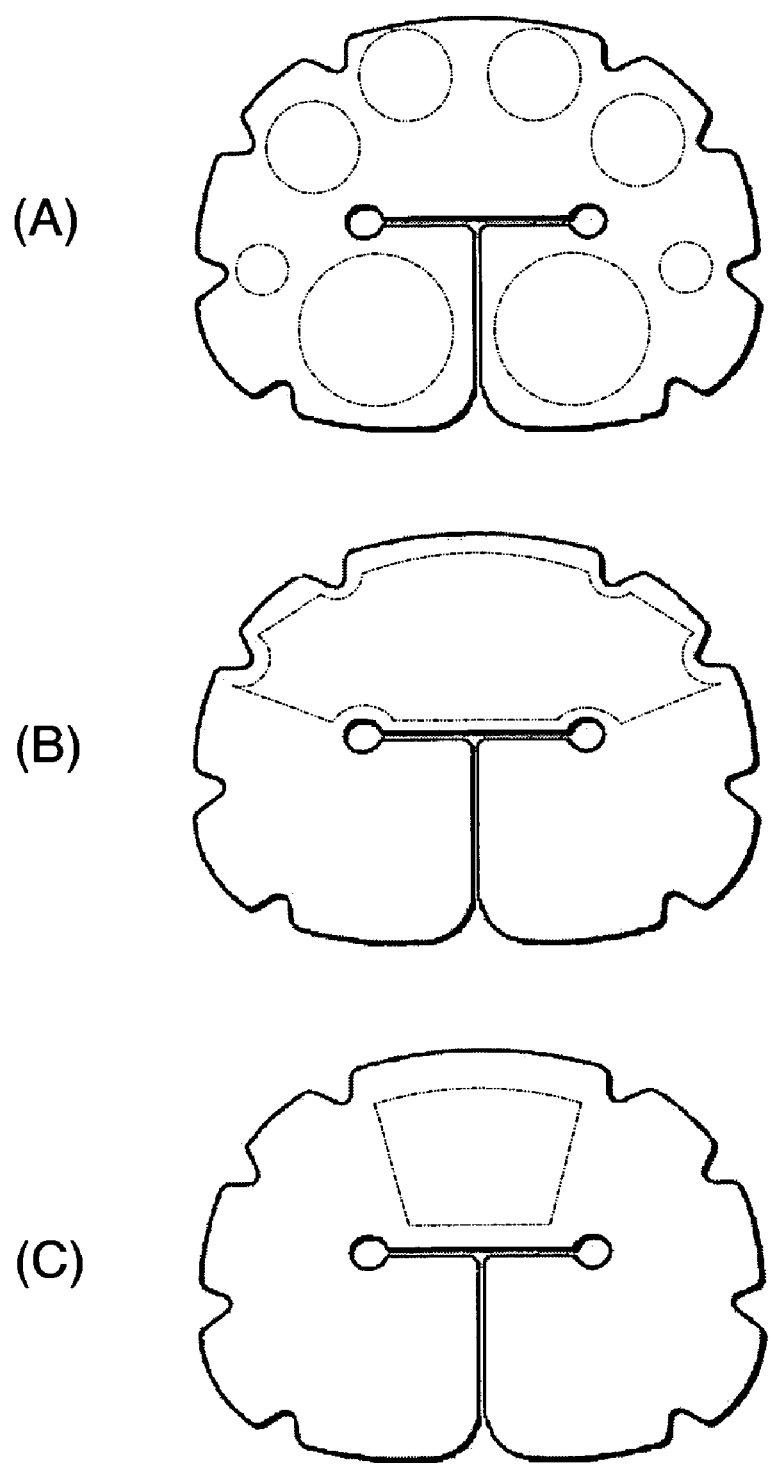
FIG. 2, embodiments A, B, and C, is a drawing of exemplary selectively expandable composite intervertebral disc prostheses according to embodiments of the invention.

In a preferred embodiment, more than one hydrophilic polymer core is positioned within the outer shell. The cores may be positioned at selected regions of the composite structures in which expansion is desired. An exemplary selectively expandable intervertebral disc prosthesis having multiple cores placed at selected positions within the outer shell is illustrated in FIG. 2, embodiment A. Embodiment A illustrates a selectively expandable composite intervertebral disc prosthesis with multiple hydrophilic polymer cores with circular cross-sections within the outer shell. The multiple hydrophilic cores are disposed at various positions within the outer shell. When they are hydrated, the cores may cause the shell to be selectively deformed at these positions.

FIG. 2, embodiments B and C, illustrate other selectively expandable composite intervertebral disc prostheses comprising an outer shell and a core comprised of a hydrophilic polymer positioned within the outer shell. In both embodiments, the core is located at the anterior portion of the intervertebral disc prosthesis. Therefore, upon hydration, the prosthesis will selectively expand at the anterior portion, which may be useful to correct and maintain proper curvature in the spine.

Figure 3:
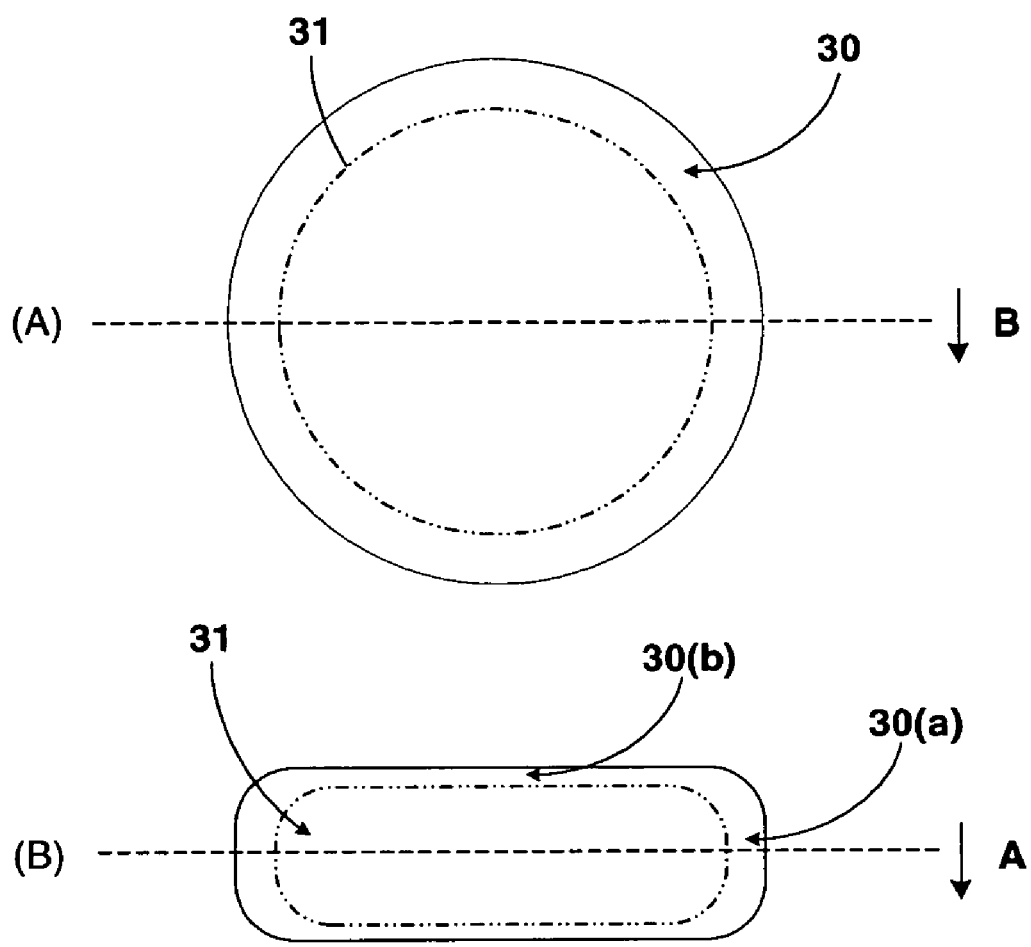
FIG. 3, embodiments A and B, is a drawing of two sectional views of an exemplary selectively expandable composite intervertebral disc prosthesis FIG. 4, embodiments A and B, is a drawing of an exemplary selectively expandable composite intervertebral disc prosthesis.

FIG. 3, embodiments A and B, illustrates another intervertebral disc prosthesis according to embodiments of the invention. An outer shell 30 and a hydrophilic core 31 positioned within the shell are provided. In embodiment B, it can be seen that the thickness of the outer shell may vary depending upon its position in the prosthesis. For example, at the periphery of the prosthesis, the outer shell 30(*a*) is thicker than it is at the top and bottom of the prosthesis 30(*b*). As mentioned, the shape of the outer shell can affect the behavior of the composite structures during expansion. For example, where the outer shell is thicker at the periphery of the composite structures than at the top and bottom, as is exemplary illustrated in FIG. 3, embodiment B, the composite structure may expand more in the vertical direction than the horizontal or peripheral direction when hydrated. Therefore, preferential expansion in the vertical direction may be achieved. In generally, varying the thickness of the outer shell depending upon its position within the device may effect the expandability of the device. Portions of the device where expansion upon hydration is desired, for example, may have a thinner outer shell, whereas portions of the device where expansion is not desired and is to be limited may have a thicker outer shell.

Another method by which the expansion of the composite structures during hydration may be controlled is by varying the concentration and composition of the non-hydrogel polymeric material and hydrophilic polymer comprising, respectively, the outer shell and the at least one core of the composite structures. For example, by diluting the hydrophilic polymer which comprises the at least one core with a non-hydrophilic polymer, the expandability of the composite structures may be decreased. Also, by mixing the non-hydrogel polymeric material comprising the outer shell with more or less compliant polymers, the expandability of the composite structures may be, respectively, increased and decreased. In a preferred embodiment, for example, the hydrophilic core may comprise from about 1% to about 50% of a non-hydrophilic polymer in order to enhance the core's mechanical properties. One skilled in the art will appreciate the wide variety of polymeric components that may be mixed with the hydrophilic polymer comprising the core and the non-hydrogel polymer material comprising the outer shell.

Another method by which the expandability of the composite structures may be regulated is by the inclusion of one or more reinforcing elements in the outer shell. Reinforcing elements applicable to the composite structures according to embodiments of the invention include, but are not limited to, metallic fibers, carbon fibers, metal meshes, and woven fiber inserts. For example, metallic, ceramic, or polymeric fibers in continuous, discontinuous, woven, non-woven, and braided fabrics may be placed on the surface of the device. Alternatively, such structures may be used as a band around the perimeter or periphery of the device. Such structures also may be embedded into the shell or core of the composite structures. One of skill in the art will appreciate other applicable reinforcing elements, in accordance with the guidelines provided herein. Generally, the reinforcing elements may be positioned at portions of the outer shell where expansion is to be limited. Therefore, the expansion of the selectively expandable composite structure may be directed by placing reinforcing elements at or in portions of the outer shell were expansion is desired to be limited or prevented.

In general, inclusion of reinforcing elements, varying the thickness of the outer shell, and varying the composition of the outer shell and/or hydrophilic core of the device may be categorized as methods to vary the modulus of elasticity of the device. Varying the modulus of elasticity of portions of the device depending upon the portions' positions in the device may be desirable as a way to encourage selective expansion upon hydration of the device. Selective expansion of implantable devices may be desirable to create structures of more complex geometry for better clinical outcomes, as discussed herein.

In another preferred embodiment, the selectively expandable composite structures may be combined with additional components to form a more complex implantable device. For example, a selectively expandable composite structure may function as the nucleus of a total disc replacement (TDR) device that comprises other components in addition to a selectively expandable composite structure. In a preferred embodiment, vertebral endplate contacting elements are positioned on the upper and lower surfaces of the device. Endplate contacting elements preferably may be composed of a medical metal or alloy and may be configured to engage the vertebral endplates of the vertebrae between which the selectively expandable composite structure is to be implanted.

Besides imparting expandability to the composite structures, the at least one hydrophilic core may act as a reservoir to retain and deliver various therapeutics, pharmaceutical agents, growth factors, and radiopaque materials. The therapeutics, pharmaceutical agents, growth factors, and radiopaque materials preferably may be controllably released from the hydrophilic core. In other words, the core may function to slowly release the materials disposed therein following implantation. Conduits, slits, pores, or a hydrophilic component in the outer shell may act to allow the therapeutics to exit the core of the composite structure. Additionally, therapeutics, pharmaceutical agents, growth factors, and radiopaque materials may be mixed with the outer shell in order to impart additional biologically advantageous characteristics to the outer shell or to aid in identifying and positioning the device during implantation.

For example, the non-hydrogel polymer materials and hydrophilic polymers may comprise therapeutics such as pharmacological agents, biological agents, and growth factors. Examples of pharmacological agents, biological agents, and growth factors include, but are not limited to, antibiotics, analgesics, anti-inflammatory drugs, steroids, anti-viral and anti-retroviral compounds, therapeutic proteins or peptides, and therapeutic nucleic acids (as naked plasmid or a component of an integrating or non-integrating gene therapy vector system).

Antibiotics useful with the selectively expandable composite structures include, but are not limited to, aminoglycosides, amoxicillin, beta-lactamases, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin. In addition, one skilled in the art of implant surgery or administrators of locations in which implant surgery occurs may prefer the introduction of one or more of the above-recited antibiotics to account for nosocomial infections or other factors specific to the location where the surgery is conducted. Accordingly, the invention further contemplates that one or more of the antibiotics recited supra, and any combination of one or more of the same antibiotics, may be included in the selectively expandable composite structures of the invention.

Immunosuppressives may be administered with the selectively expandable composite structures according to the embodiments. Suitable immunosuppressive agents that may be administered include, but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents that may be administered in combination with the selectively expandable composite structures include, but are not limited to, prednisolone, methotrexate, thalidomide, methoxsalen, rapamycin, leflunomide, Bredinin™ (mizoribine), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus). Other drugs useful with the composite structures include anti-cytokines such as anti-tumor necrosis factor alpha (anti-TNF alpha), anti-interleukin 2 (anti-IL2), anti-IL4, anti-IL10, anti-IL18, etc.

Therapeutic polynucleotides or polypeptides (hereinafter "therapeutics") may be used with the selectively expandable composite structures. The therapeutics may be administered as proteins, peptides, and therapeutic nucleic acids, and may be administered as full length proteins, mature forms thereof, and domains thereof, as well as the polynucleotides encoding the same. Examples of therapeutic polypeptides include, but are not limited to, Bone Morphogenetic Proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-bs), including TGF-b-1, TGF-b-2, and TGF-b-3; and Platelet Derived Growth Factors (PDGFs), including PDGF-A, PDGF-B, PDGF-C, and PDGF-D. The polynucleotides encoding the same also may be administered as gene therapy agents.

In a particularly preferred embodiment, the selectively expandable composite structures may comprise antagonists to either the myelin-associated glycoprotein (MAG) or Nogo-A, the largest transcript of the recently identified nogo gene (formerly called NI-220), which are both present in CNS myelin and have been characterized as potent inhibitors of axonal growth. For example, Nogo-A acts as a potent neurite growth inhibitor in vitro and represses axonal regeneration and structural plasticity in the adult mammalian CNS in vivo. In another embodiment, antagonists to both MAG and Nogo-A are co-administered to the patient. In this preferred embodiment, the selectively expandable composite structures of the invention are used as implants for intervertebral discs that are adjacent locations of spinal cord injury, and may also replace a damaged or infected native nucleus pulposus. In this embodiment, the inhibitory activity of the antagonist(s) to the activity of MAG and Nogo-A may aid in the regeneration of damaged spinal nerve tissue, and the selectively expandable composite structure serves as a local reservoir of therapeutic antagonist(s) to aid in the growth of damaged spinal tissue. Antagonists of MAG and Nogo-A may take the form of monoclonal antibodies, antisense molecules, small molecule antagonists, and any other forms of protein antagonists known to those of skill in the art.

In this embodiment, therapeutic polypeptides or polynucleotides of Ninjurin-1 and Ninjurin-2 may further be administered alone or in conjunction with one or more MAG or Nogo-A antagonists, as a component of the selectively expandable composite structures. Ninjurin-1 and Ninjurin-2 are believed to promote neurite outgrowth from primary cultured dorsal root ganglion neurons. Ninjurin-1 is a gene that is up-regulated after nerve injury both in dorsal root ganglion (DRG) neurons and in Schwann cells. The full-length proteins, mature forms, or domains of the full-length proteins thereof may be administered as therapeutics, as well as the polynucleotides encoding the same.

Embodiments of the invention also include a method of treating spinal cord injury using the selectively expandable composite structures described herein as a reservoir for therapeutic agents that promote the growth of injured spinal cord tissue or damaged nerves. The method includes administering at least one or more, including all, of the above-recited therapeutics as a component of the selectively expandable composite structures of the invention. In one embodiment, the non-hydrogel polymer material and hydrophilic polymer may be admixed with the therapeutic agents. In another embodiment of the invention, the therapeutic agents are applied to the selectively expandable composite structures prior to implantation of the structures. The therapeutic agents may be administered to the selectively expandable composite structures in any number of suitable fluids, such as for example, water, saline solution, and calcium phosphate solution.

Methods of producing therapeutic polynucleotides and polypeptides that may be co-administered with the selectively expandable composite structures are well known to one of skill in the art. Vectors containing the therapeutic polynucleotides recited supra, host cells, and the production of therapeutic polypeptides by recombinant techniques can be used to make the therapeutic polynucleotides and polypeptides. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells. Useful vectors include, but are not limited to, plasmids, bacteriophage, insect and animal cell vectors, retroviruses, cosmids, and other single and double-stranded viruses.

The polynucleotide insert may be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs may further contain sites for transcription initiation, termination, origin of replication sequence, and, in the transcribed region, a ribosome binding site for translation. The coding portion of the transcripts expressed by the constructs preferably may include a translation initiating codon at the beginning and a termination codon (UAA, UGA or UAG) appropriately positioned at the end of the polypeptide to be translated.

The expression construct may further contain sequences such as enhancer sequences, efficient RNA processing signals such as splicing and polyadenylation signals, sequences that enhance translation efficiency, and sequences that enhance protein secretion.

Expression systems and methods of producing therapeutics, such as recombinant proteins or protein fragments, are well known in the art. For example, methods of producing recombinant proteins or fragments thereof using bacterial, insect or mammalian expression systems are well known in the art. (See, e.g., Molecular Biotechnology: Principles and Applications of Recombinant DNA, B. R. Glick and J. Pasternak, and M. M. Bendig, Genetic Engineering, 7, pp. 91–127 (1988), for a discussion of recombinant protein production).

The expression vectors preferably will include at least one selectable marker. Such markers include dihydrofolate reductase, G418 or neomycin resistance for eukaryotic cell culture and tetracycline, kanamycin, or ampicillin resistance genes for culturing in *E. coli* and other bacteria. Representative examples of appropriate host cells for expression include, but are not limited to, bacterial cells such as *E. coli, Streptomyces* and *Salmonella typhimurium* cells; fungal cells such as *Pichia, Saccharomyces* and other yeast cells; insect cells such as *Drosophila* S2 and *Spodoptera* Sf9 and Sf21 cells; animal cells such as CHO, COS, 293, and Bowes melanoma cells; and plant cells. Appropriate culture mediums and conditions for the above-described host cells are known in the art.

Examples of vectors for use in prokaryotes include pQE30Xa and other pQE vectors available as components in pQE expression systems (commercially available from QIAGEN, Inc., Valencia, Calif.); pBluescript vectors, Phagescript vectors, pNH8A, pNH16a, pNH18A, and pNH46A (commercially available from Stratagene Cloning Systems, Inc., La Jolla, Calif.); and Champion™, T7, and pBAD vectors (commercially available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, and other methods. Such methods are described in many standard laboratory manuals, such as Davis et al., Basic Methods In Molecular Biology (1986).

A polypeptide of an embodiment can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") may be employed for purification.

In another embodiment, therapeutic agents can be produced using bacterial lysates in cell-free expression systems that are well known in the art. Commercially available examples of cell-free protein synthesis systems include the EasyXpress System (commercially available from Qiagen, Inc., Valencia, Calif.).

Therapeutics also can be recovered from products of chemical synthetic procedures and products produced by recombinant techniques from a prokaryotic or eukaryotic host, including, for example, bacterial, yeast, higher plant, insect, and mammalian cells.

Depending upon the host employed in a recombinant production procedure, therapeutics may be glycosylated or may be non-glycosylated. In addition, therapeutics also may include an initial modified methionine residue, in some cases as a result of host-mediated processes. Thus, it is known that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

Therapeutics also may be isolated from natural sources of polypeptide. Therapeutics may be purified from tissue sources, preferably mammalian tissue sources, using conventional physical, immunological and chemical separation techniques known to those of skill in the art. Appropriate tissue sources for the desired therapeutics, or other techniques for obtaining the recited therapeutics such as PCR techniques, are known or are available to those of skill in the art.

Embodiment of the invention also provide a method of treating a disease or disorder associated with the spine. The method comprises providing a selectively expandable composite intervertebral disc prosthesis as described herein. The prosthesis may be dehydrated in order to attain a smaller volume and reduced profile. Then, the prosthesis may be inserted into an intervertebral disc space and allowed to re-hydrate therein in order to expand and reach a final configuration. A suitable method of delivering or implanting a prosthesis according to embodiments of the invention is described in, for example, U.S. Patent Application Publication No. 2004/0117019 (application Ser. No. 10/717,687), the disclosure of which is incorporated by reference herein in its entirety.

In one embodiment of the invention, a dysfunctional intervertebral disc is accessed surgically, preferably using minimally invasive techniques, and at least a portion of the native nucleus pulposus material and any free disc fragments are removed. Subsequently, the selectively expandable composite intervertebral disc prosthesis may be delivered to the at least partially evacuated disc space. Delivery of the prosthesis to the at least partially evacuated disc space preferably may be achieved, for example, using minimally invasive surgical techniques and devices. For example, a prosthesis according to embodiments of the invention may be delivered via a cannula to the at least partially evacuated disc space. Dehydration of the prosthesis prior to implantation may facilitate the use of minimally invasive surgical techniques because dehydration may reduce the volume and profile of the prosthesis. Alternatively, the prosthesis may be delivered to the at least partially evacuated disc space in a more direct manner absent a cannula. The appropriate delivery method may be selected by a suitably skilled surgeon.

Upon implantation, the selectively expandable composite intervertebral disc prosthesis may be re-hydrated by endogenous fluids in the body. Alternatively, a hydrating fluid may be delivered to the implanted prosthesis in order to aid hydration. Appropriate hydrating fluids include, but are not limited to, water, saline solution, and calcium-phosphate based solutions. During re-hydration, the prosthesis may selectively expand to reach its final configuration. In a preferred embodiment, the selectively expandable composite prosthesis expands to a greater height in its anterior than its posterior portion, or visa versa. This may be advantageous in order to correct or maintain curvature of the section of the spine in which the prosthesis is to be implanted.

In a preferred embodiment, following hydration of the selectively expandable intervertebral disc prosthesis, the hydrated prosthesis substantially fills the at least partially evacuated cavity of the intervertebral disc space. In order to accomplish this, it may be desirable to measure the volume of the intervertebral disc space prior to implantation of the prosthesis. Following measurement, a prosthesis with a hydrated volume substantially similar to the volume of the intervertebral disc space may be chosen for implantation. The intervertebral disc prosthesis preferably occupies at least 50% of the evacuated intervertebral disc space, more preferably 70% of the evacuated intervertebral disc space, even more preferably 80% of the intervertebral disc space, even more preferably 90% of the evacuated intervertebral disc space, and most preferably 99% or more of the evacuated intervertebral disc space following expansion.

Besides the volume of the intervertebral disc space in which the prosthesis is to be implanted, other dimensions such as the disc space height and width may be measured in order to choose a prosthesis of the correct size and geometry for the disc space. The size of the selectively expandable prosthesis, when fully hydrated, can be varied for different individuals. A typical size of an adult intervertebral disc is roughly about 3.5 cm in the semi-minor axis, about 5.5 cm in the semi-major axis and about 1.2 cm in thickness. The embodiments contemplate numerous sizes for the prosthesis to accommodate different sizes of individual patients, relative to the typical size set forth above. Using the guidelines provided herein, skilled artisans are capable of determining an appropriately sized prosthesis, depending on the size and age of the patient, as well as on the amount of disc material removed or evacuated from the disc space.

In a preferred embodiment, the selectively expandable composite structure may be impregnated with a radiopaque material or solution prior to implantation. Alternatively, the composite structure may comprise radiopaque markers embedded therein or attached to its surface. Radiopaque materials, solutions, and markers may be useful to aid in positioning or orienting of the device during and following implantation. For example, the region in which the composite structure is to be implanted (e.g., the intervertebral disc space) may be fluoroscopically imaged during the implantation procedure in order to determine how the device's position and orientation. Then, the position or orientation of the device may be altered if it is found that the device is not yet positioned or oriented correctly. The process of imaging and re-positioning may be repeated as needed until the composite structure is correctly situated in the implantation region.

In one embodiment, the selectively expandable intervertebral disc prosthesis is useful in the replacement of native nucleus pulposus materials. In another embodiment, the prosthesis is useful in the prevention or treatment, or for aiding in the prevention or treatment, of diseases and/or disorders associated with the spinal column. Non-limiting examples of diseases and/or disorders that the prostheses provided by embodiments of the invention are useful in preventing or treating include, but are not limited to: bulging disc(s); herniated disc(s); spinal injury due to trauma; age-related degeneration or failure of spinal column components (namely intervertebral disc(s)); spinal instability; discogenic back pain; intervertebral osteochondrosis; spondylolisthesis; spinal infection; spinal tumors; and arthritis of the spine.

In an additional embodiment, the selectively expandable intervertebral disc prostheses are packaged in kits under sterile conditions prior to implantation into a patient. The prostheses may be included as a component of a surgical kit for implanting the device, along with other surgical tools or instruments. Preferably, the kit comprises the selectively expandable prosthesis together with a minimally invasive delivery apparatus or system.

The invention will now be described in more detail with reference to the following prophetic example.

EXAMPLE

Figure 4:
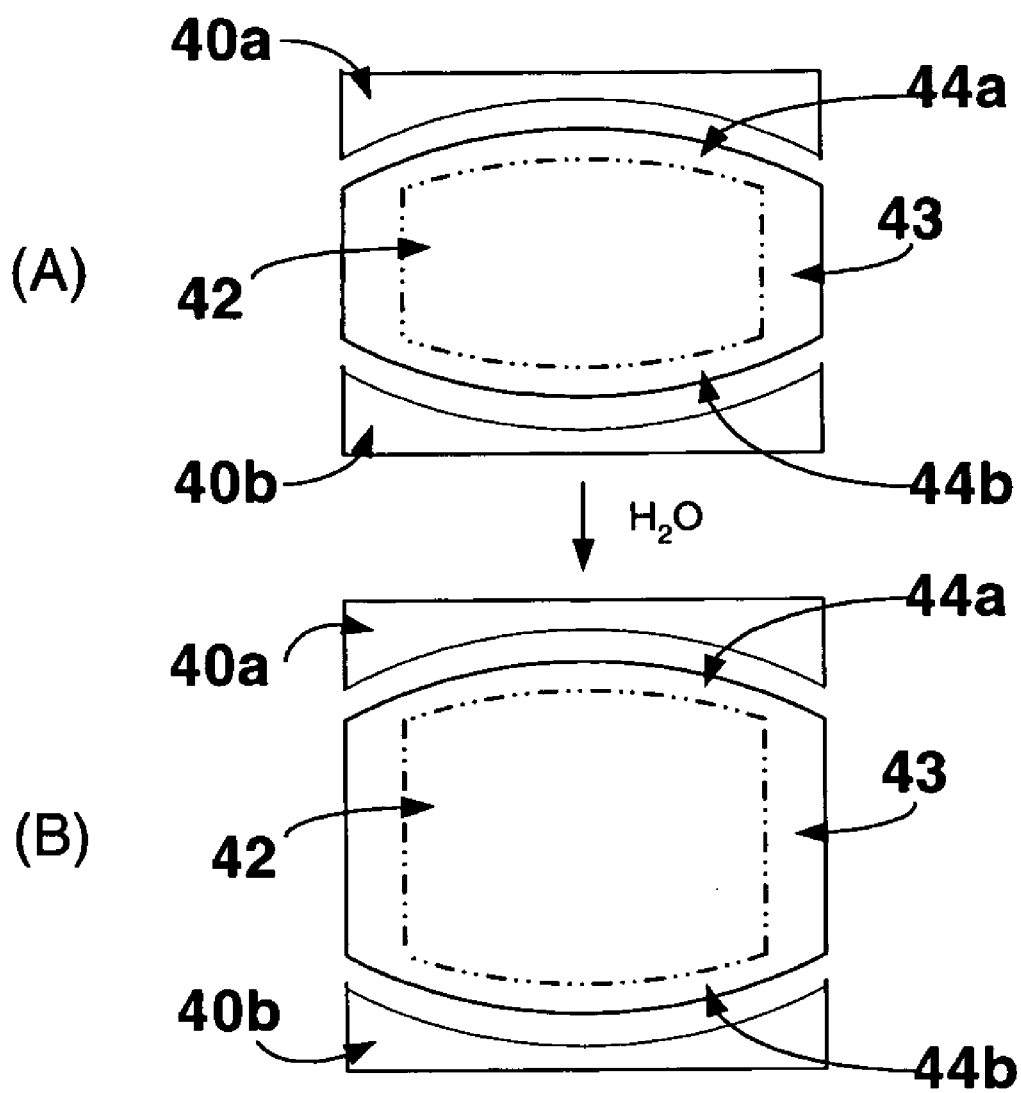

A selectively expandable composite structure according to FIG. 4, embodiments A and B, may be provided. The composite structure may comprise a hydrophilic core 42 inside of an outer shell having a differential composition. The top 44a and bottom 44b of the outer shell may be comprised of a ultra high molecular weight polyethylene (UHMWPE). These surfaces may act as articulating surfaces. The periphery or sides of the outer shell 43 may be comprised of a more elastic composition. Metallic endplates 40a and 40b may be provided to act as vertebral endplate engaging plates. Upon hydration, the more elastic periphery of the outer shell 43 may allow the hydrophilic core 42 to expand, thereby increasing the height of the device and pushing the endplates 40a and 40b against the adjacent vertebrae.

The foregoing detailed description is provided to describe the invention in detail, and is not intended to limit the invention. Those skilled in the art will appreciate that various modifications may be made to the invention without departing significantly from the spirit and scope thereof.

What is claimed is:

1. A selectively expandable composite intervertebral disc prosthesis, comprising:
    an outer shell comprised of a non-hydrogel polymer material;
    at least one core positioned within the outer shell, the core comprised of a hydrophilic polymer; and
    at least one conduit comprised of a hydrophilic polymer that connects the at least one core with the surface of the prosthesis;
    where the at least one core expands upon hydration, thereby deforming the outer shell.

2. The device of claim 1, wherein the outer shell comprises a plurality of perforations of sufficient size and number to permit fluids to percolate through the shell and contact at least a portion of the at least one core.

3. The device of claim 1, wherein the outer shell is at least partially porous.

4. The device of claim 1, further comprising a hydrophilic component in the outer shell.

5. The device of claim 4, wherein the hydrophilic component in the outer shell is selected from the group consisting of polyvinyl alcohol, polyacrylic acid, poly(acrylonitrile-acrylic acid), polyacrylamides, poly(N-vinyl-2-pyrrolidone), polyurethanes, polyethylene glycol, polyethyleneoxide, poly(N-vinyl-2-pyrrolidone), polyacrylates, poly(2-hydroxy ethyl methacrylate), copolymers of acrylates with N-vinyl pyrrolidone, N-vinyl lactams, acrylamide, and mixtures and combinations thereof.

6. The device of claim 1, wherein the outer shell is comprised of a material selected from the group consisting of silicone, polyurethanes, silicone polyurethane copolymers, polyolefins, thermoplastic elastomers, thermoset elastomers, thermoplastic polymers, thermoset polymers, polybutadiene, polyisobutylene, polyisoprene, neoprene, nitrile, vulcanized rubber, and mixtures and combinations thereof.

7. The device of claim 6, wherein the outer shell is comprised of a thermoplastic silicone polyurethane copolymer.

8. The device of claim 7, wherein the thermoplastic silicone polyurethane copolymer is selected from the group consisting of silicone polyetherurethanes; silicone polycarbonateurethane; silicone poly(tetramethylene-oxide) (PTMO) polyether-based aromatic silicone polyurethanes; silicone PTMO polyether-based aliphatic polyurethanes; silicone polyurethane ureas; and mixtures and combinations thereof.

9. The device of claim 1, wherein the hydrophilic polymer is selected from the group consisting of polyacrylamide; polyacrylic acid; polyvinylpyrrolidone; copolymers of ethyleneoxide and propyleneoxide or hyaluronic acid; collagen; gelatin; albumin; keratin; elastin; silk; hyaluronic acid and derivatives thereof; proteoglycan; glucomannan gel; polysaccharides; polyelectrolytes; and mixtures and combinations thereof.

10. The device of claim 9, wherein the polyelectrolytes are selected from the group consisting of proteins, nucleic acids, sulfonated styrene, polyacrylic acids, carboxymethylcellulose, polyacrylic acid, xantham gum, pectins, polystyrene sulfate, polymethacrylic acid, polyallylamine hydrochloride, carrageenan, and mixtures and combinations thereof.

11. The device of claim 1, wherein the hydrophilic polymer is selected from the group consisting of polyvinyl alcohol, polyacrylic acid, poly(acrylonitrile-acrylic acid), polyacrylamides, poly(N-vinyl-2-pyrrolidone), polyurethanes, polyethylene glycol, polyethyleneoxide, poly(N-vinyl-2-pyrrolidone), polyacrylates, poly(2-hydroxy ethyl methacrylate), copolymers of acrylates with N-vinyl pyrrolidone, N-vinyl lactams, acrylamide, and mixtures and combinations thereof.

12. The device of claim 1, further comprising at least one additive impregnated in the core, wherein the additive is selected from the group consisting of sodium chloride, calcium chloride, magnesium chloride, magnesium sulfate, potassium sulfate, potassium chloride, sodium sulfate, sodium acetate, ammonium phosphate, ammonium sulfate, calcium lactate, magnesium succinate, sucrose, glucose, and fructose.

13. The device of claim 1, wherein the prosthesis has a height within the range of from about 3 millimeters to about 15 millimeters.

14. The device of claim 1, wherein the prosthesis has a volume within the range of from about 0.5 milliliters to about 8 milliliters.

15. The device of claim 1, wherein the outer shell is substantially deformable in a direction parallel to the spine during expansion of the at least one core, and substantially less deformable in a direction perpendicular to the spine during expansion of the at least one core, when the device is oriented in its intended implanted orientation.

16. The device of claim 1, wherein the modulus of elasticity of the outer shell varies depending upon its position in the device.

17. The device of claim 1, wherein the thickness of the outer shell varies depending upon its position in the device.

18. The device of claim 1, wherein the composition of material comprising the outer shell varies depending upon its position in the device.

19. The device of claim 1, wherein one or more reinforcing elements selected from the group consisting of metallic, polymeric, ceramic, carbon fibers, mesh, and fabrics are positioned at or in portions of the outer shell where expansion is desired to be limited.

20. The device of claim 1, wherein the at least one core is in a physical configuration selected from the group consisting of a single piece, multiple pieces, chunks, granules, flakes, pellets, cylinders, strips, spheres, microspheres, powders, beads, capsules, particulates, and mixtures and combinations thereof.

21. The device of claim 1, wherein at least a portion of the core is porous, and the porous portion of the core comprises no more that about 75% by volume of voids.

22. The device of claim 1, wherein the volume of the device following hydration is no more that about three times the volume of the device in a de-hydrated state.

23. The device of claim 1, further comprising vertebral endplate contacting elements attached to the top and bottom of the device.

24. The device of claim 1, wherein the cross-sectional shape of the device is selected from the group consisting of kidney-shaped, C-shaped, oval-like, spherical, rectangular, square, cylindrical, capsule, U-shaped, V-shaped, X-shaped, and "O" or donut shaped.

25. The device of claim 1, further comprising at least one therapeutic agent, pharmaceutical agent, or growth factor impregnated in the core.

26. The device of claim 1, further comprising at least one therapeutic agent, pharmaceutical agent, or growth factor impregnated in or coated on the outer shell.

27. The device of claim 1, further comprising a radiopaque material or solution impregnated in the device.

28. The device of claim 1, further comprising a radiopaque marker embedded in the device or attached to its surface.

29. A method of treating or preventing a disease or disorder associated with the spine, comprising:
providing a selectively expandable composite intervertebral disc prosthesis as in claim 1;
substantially dehydrating the prosthesis;
inserting the prosthesis into an intervertebral disc space; and
allowing the prosthesis to re-hydrate in the intervertebral disc space.

30. The method of claim 29, wherein the prosthesis shrinks upon dehydration and expands upon re-hydration.

31. The method of claim 29, wherein the prosthesis expands to a greater height upon re-hydration in its anterior portion than in its posterior portion.

32. The method of claim 29, further comprising delivering a material selected from the group consisting of water or saline solution to the prosthesis following insertion.

33. The method of claim 32, further comprising mixing with the water or saline solution a material selected from the group consisting of radiopaque agents, therapeutic agents, growth factors, pharmaceutical agents, and mixtures and combinations thereof.

34. The method of claim 29, further comprising surgically evacuating at least a portion of the nucleus pulposus material and any free disc fragments from the intervertebral disc space prior to inserting the prosthesis into the intervertebral disc space.

35. The method of claim 29, further comprising measuring the volume of the intervertebral disc space prior to inserting the prosthesis into the intervertebral disc space.

36. The method of claim 29, wherein inserting the prosthesis is accomplished by the use of minimally invasive surgical techniques.

37. The method of claim 29, wherein the disease or disorder is selected from the group consisting of: bulging discs; herniated discs; spinal injury due to trauma; age-related degeneration or failure of spinal column components; spinal instability; discogenic back pain; intervertebral osteochondrosis; spondylolisthesis; spinal infection; spinal tumors; arthritis of the spine; and combinations thereof.

38. A selectively expandable composite intervertebral disc prosthesis, comprising:
   an outer shell comprised of a non-hydrogel polymer material; and
   at least one core positioned within the outer shell, the core comprised of a hydrophilic polymer;
   where at least a portion of the core is porous, and the porous portion of the core comprises no more that about 75% by volume of voids; and
   where the at least one core expands upon hydration, thereby deforming the outer shell.

39. A method of treating or preventing a disease or disorder associated with the spine, comprising:
   providing a selectively expandable composite intervertebral disc prosthesis as in claim 38;
   substantially dehydrating the prosthesis;
   inserting the prosthesis into an intervertebral disc space; and
   allowing the prosthesis to re-hydrate in the intervertebral disc space.

\* \* \* \* \*